(12) United States Patent
Shana et al.

(10) Patent No.: US 6,687,004 B1
(45) Date of Patent: Feb. 3, 2004

(54) OPTICAL SENSOR FOR OPAQUE AND NON-OPAQUE MATERIALS

(75) Inventors: Zack A. Shana, Franklin, WI (US); Carljon Mercier, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 0 days.

(21) Appl. No.: 09/425,458

(22) Filed: Oct. 22, 1999

(51) Int. Cl.[7] .................. G01N 21/00; G01N 21/41
(52) U.S. Cl. ................. 356/436; 440/128; 440/134
(58) Field of Search ..................... 356/436–440, 356/128, 134

(56) References Cited

U.S. PATENT DOCUMENTS

| | | |
|---|---|---|
| 3,549,893 A | 12/1970 | Gibbs |
| 3,636,360 A | 1/1972 | Oishi et al. |
| 3,908,129 A | 9/1975 | Akers |
| 4,100,797 A | 7/1978 | Oberhardt et al. |
| 4,240,747 A | 12/1980 | Harmer |
| 4,699,511 A | 10/1987 | Seaver |
| 4,710,643 A | 12/1987 | Schmukler et al. |
| 4,829,448 A | 5/1989 | Balding et al. |
| 4,935,621 A | 6/1990 | Pikulski |
| 4,979,643 A | 12/1990 | Lipisko et al. |
| 4,989,452 A | 2/1991 | Toon et al. |
| 5,355,735 A | 10/1994 | Miller et al. |
| 5,402,242 A * | 3/1995 | Nakano ............. 356/436 |
| 5,422,495 A | 6/1995 | Cohn |
| 5,427,920 A | 6/1995 | Berndt et al. |
| 5,641,458 A | 6/1997 | Shockley, Jr. et al. |
| 5,724,142 A | 3/1998 | Kaminski et al. |
| 5,729,333 A | 3/1998 | Osten et al. |
| 5,831,268 A | 11/1998 | Morita et al. |
| 5,870,185 A | 2/1999 | See et al. |

FOREIGN PATENT DOCUMENTS

| | | |
|---|---|---|
| EP | 185285 | 6/1986 |
| EP | 0597584 | 5/1994 |
| EP | 0682242 | 11/1995 |
| JP | 59122991 | 7/1984 |
| JP | 04009749 | 1/1992 |
| WO | WO 90/04165 | 4/1990 |

OTHER PUBLICATIONS

Burr–Brown "Monolithic Photodiode and Single–Supply Transimpedance Amplifier", Mar. 1988, pp. 1–11.
Cole Parmer, Out–of–Liquid Sensor EW–77095–50, www.coleparmer.com, date not available.
Masterflex, Sensors, pp. 1383, date not available.
Cole Parmer, Liqui–Sense® Fluid Monitoring System, pp. 826–827, date not available.
Cole Parmer, Liqui–Sense Controller EW–77096–00, www.coleparmer.com, date not available.
Cole Parmer, Liqui–Sense Controller EW–77096–05, www.coleparmer.com. date not available.
Cole–Parmer 77095–50 Out–of–liquid sensor, Operating Instructions, date not available.

* cited by examiner

*Primary Examiner*—Frank G. Font
*Assistant Examiner*—Amanda Merlino
(74) *Attorney, Agent, or Firm*—Foley & Lardner

(57) ABSTRACT

A sensor is capable of detecting clear or opaque materials. The sensor can be disposed around a clear tube which carries a material such as liquid. The sensor utilizes a thin beam light source and a wide area photo detector. A window comparator determines the presence or absence of a material such as liquid.

20 Claims, 2 Drawing Sheets

OPTICAL SENSOR FOR OPAQUE AND NON-OPAQUE MATERIALS

FIELD OF THE INVENTION

The present invention is related to a; sensor. More particularly, the present invention is related to a sensor capable of detecting the presence of non-opaque (e.g., translucent, clear or transparent) and opaque (non-transparent) materials.

BACKGROUND OF THE INVENTION

Detecting the presence of materials, such as, liquids can be done by either non-invasive or invasive methods. For example, a liquid may be transported under pressure through conduits or tubing within a system, such as an automobile cooling system, an industrial cleaning system, or a blood purification system. If a portion of a conduit within such a system is transparent, the presence of liquid within the conduit may be optically detected non-invasively (i.e. by apparatus located external to the conduit).

In other cases, use of a conduit may not be feasible, in which case liquids may be detected invasively (e.g., by bringing the sensor into direct contact with the liquid). For example, if ground water is believed to be contaminated with gasoline or oil, sensors may be lowered through bore holes into direct contact with the ground water. Direct contact often exposes the sensor to harmful environments and makes repair and retrofitting of sensors in existing systems more difficult. Further, to protect the sensor from corrosion (e.g. if the liquid to be detected is corrosive) and prevent contamination of the liquid by the sensor, an invasive system often requires an expensive housing made of materials such as stainless steel.

Non-invasive sensor systems often employ a photo detector and a light source aligned such that light from the light source passes through the liquid medium and is detected by the photo detector. Typically, such sensor systems require critical and time-consuming alignment of the source and detector. Because a liquid has a different refractive index than air, light transmitted through the medium is refracted to a different position depending on the presence or absence of liquid. Thus, the detector must be aligned to compensate for refraction related to the detected medium. Also, as light passing through a translucent medium is passed at an angle related to the refractive properties of the medium, critical and time-consuming alignment must be repeated each time a new medium is to be detected. To avoid repetition of the alignment process, additional detectors must be located at each location of possible refraction. Additional sensors increase both initial and recurring system costs. Further, each additional sensor must be carefully aligned with respect to the light source. Notably, a physical jarring may misalign the components requiring the alignment process to be repeated. In addition to alignment considerations, the sensitivity of the sensors is related to the transparency of the medium; the less transparent the medium, the less sensitive the detector. Thus, sensor sensitivity often must be adjusted for each medium to be detected.

Other types of sensors—typically non-invasive—direct a light source directly through the medium to a detector (e.g., not at an angle). These sensors, however, depend on the refractive properties of a present liquid to concentrate light onto the detector which measures the intensity of light impinging thereon. However, the less transparent the liquid, the less light will reach the detector; thus light intensity detected is also a function of the transmissive characteristics of the medium to be detected. These sensors are inherently less sensitive in detecting non-transparent (e.g., opaque) liquids, and need to be re-calibrated to detect materials with different transmissive characteristics. Therefore, detectors must be calibrated to detect either the presence of a clear (e.g., non-opaque) liquid or the presence of a substantially opaque liquid. Liquid detectors which are configured to detect a clear liquid must be reconfigured to detect an opaque liquid.

Thus, there is a need for an inexpensive, sensitive, easily-calibrated sensor or method which lends itself to non-invasively detecting the presence of a material. Further still, there is a need for a sensor or method of detecting a material which is resistant to mis-alignment of its components. Even further still, there is a need for a clear and opaque material detectors which are configured to optically detect a clear and opaque materials without recalibration.

SUMMARY OF THE INVENTION

An exemplary embodiment relates to an apparatus for detecting a material in a translucent conduit. The apparatus includes a light source and a light detector. The light source generates a narrow-beam of light and is disposed adjacent an outside surface of the conduit. The light detector has an active surface disposed adjacent the conduit along an axis defined by the light source. The light detector is operable to detect the surface area of light which impinges on the active surface and provides an output signal proportional thereto. The light from the light source is refracted by the material in the conduit so the detector provides an output signal proportional to the surface area of the impinging light.

Another embodiment in the invention relates to a method of detecting a material in a translucent conduit. The method includes steps of providing a narrow beam of light through the conduit, detecting light from the conduit, and determining a presence of the material in the conduit. The light from the conduit is detected with an active surface. The active surface provides an output signal proportional to the surface area of the light on the active surface. The presence of material in the conduit is determined in response to the output signal being above a threshold window or below the threshold window.

Yet another embodiment relates to a system for detecting presence of a material. The system includes a first translucent surface, a second translucent surface substantially in opposition to the first translucent surface, a narrow beam light source, and a light detector. The material is located between the first translucent surface and the second translucent surface. The light source is disposed adjacent the first surface. The light detector has an active surface disposed adjacent the second surface and along an axis defined by the light in substantial apposition to the light source. The light detector is operable to detect the surface area of light which impinges on the active surface and to provide an output signal proportional thereto. The light from the light source which patches through the material interposed between the first and second surfaces is refracted and impinges on the active surface. The output signal indicates a presence of the material when the output signal is above or below a threshold window.

BRIEF DESCRIPTION OF THE DRAWINGS

The invention will hereafter be described with reference to the accompanying drawings, wherein like numerals denote like elements, and.

DETAILED DESCRIPTION OF THE PREFERRED EXEMPLARY EMBODIMENTS

Figure 1:
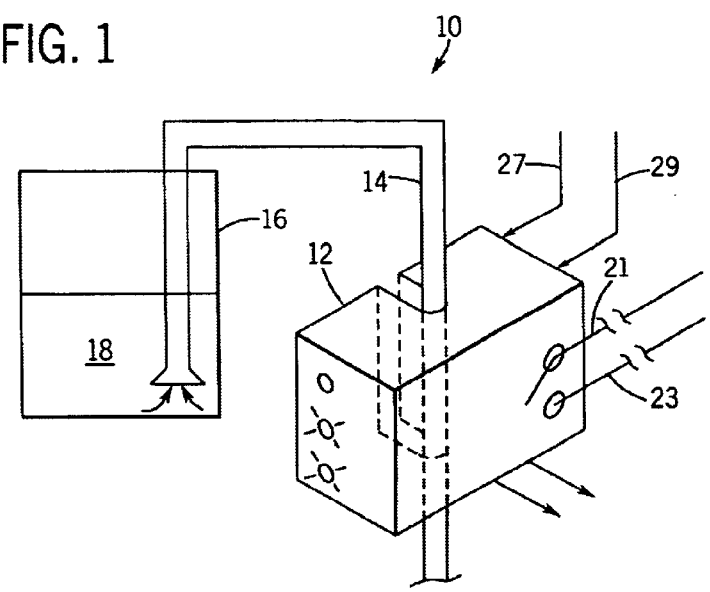
FIG. 1 is a general block diagram of an environment including a material detection sensor system.

With reference to FIG. 1, environment 10 includes a tank or a container 16 in communication with a conduit or tube 14. Container 16 can store a variety of materials, such as, a liquid 18. A material or liquid detection system 12 is disposed proximate to a tube 14. System 12 senses the presence or absence of liquid 18 in tube 14.

Environment 10 can be a truck tanker system, a detergent system, blood purification system, a wafer system, an oil system, a material handling system, or other apparatus which transports or stores material. As an example, environment 10 can be a commercial laundering facility where liquid 18 can be detergent, soaps, bleach, or other laundering material.

Liquid 18 can be an opaque or non-opaque (e.g., translucent) material. Examples of liquid 18 include: chlorine, hydroxide, a strong oxide liquid, bleach, water softener, acid, milk, water, foam, or other liquid. In addition, liquid 18 can also be a non-opaque or opaque solid material, such as, a granular material or a liquid including a solid material, which can flow through tube 14. Tube 14 is preferably translucent or has a translucent portion located proximate to system 12.

As shown in FIG. 1, liquid detection system 12 is configured for optical non-invasive detection of liquid 18 in tube 14. Alternatively, system 12 could be disposed within tube 14 to invasively detect liquid 18. Whether configured to detect invasively or non-invasively, liquid detection system 12 can advantageously detect both opaque and non-opaque liquids 18 in tube 14.

System 12 provides an output signal at terminals 21 and 23 indicating the presence or absence of liquid 18 in tube 14. Further, inputs 21 and 23 can be a transistor-to-transistor logic (TTL) interface. System 12 can be supplied with electrical power at inputs 27 and 29. Preferably, inputs 27 and 29 receive low voltage AC or DC power. The sensing or detecting operation of system 12 is discussed in more detail below with reference to FIG. 2.

Figure 2:
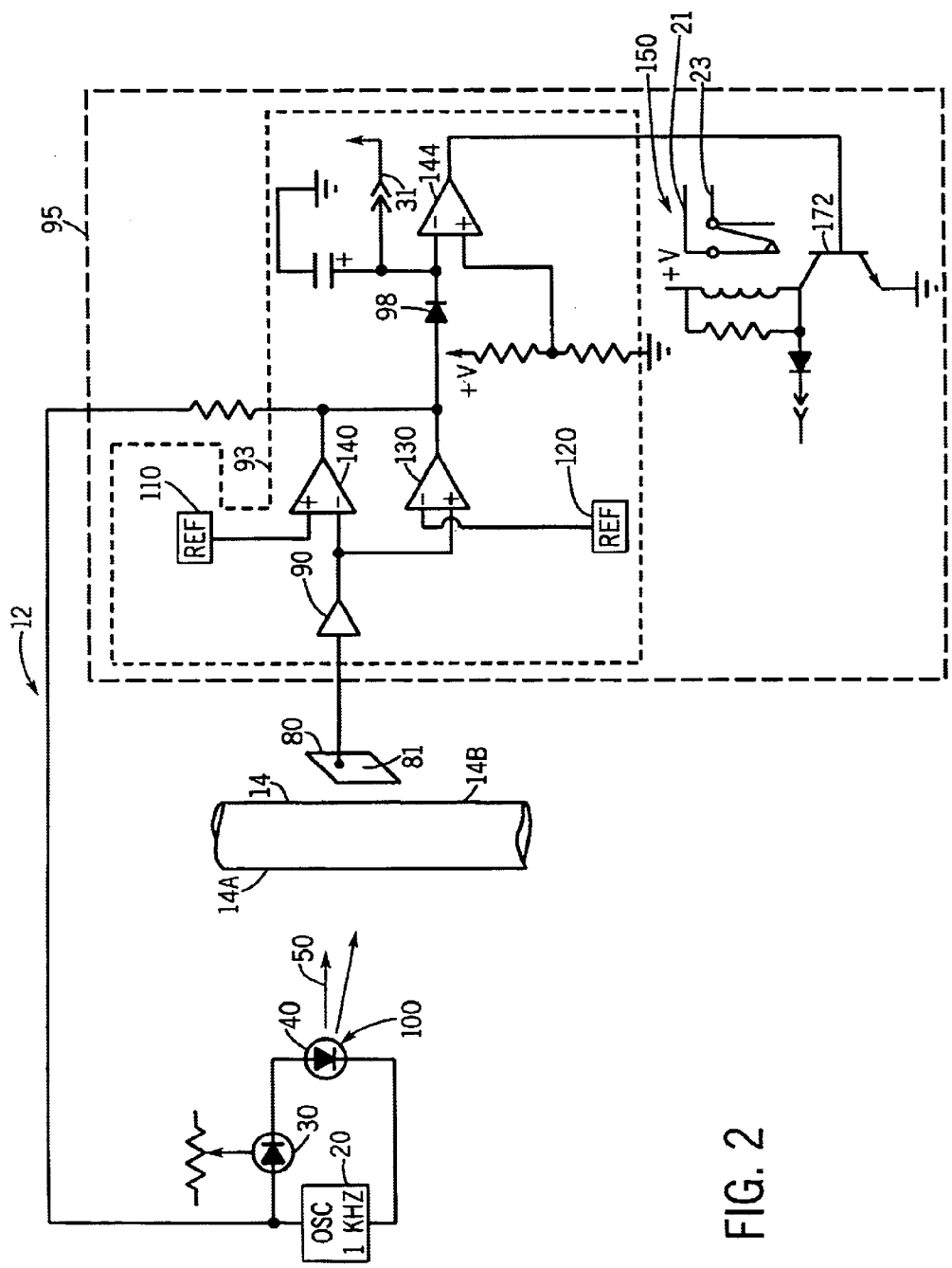
FIG. 2 is a detailed electrical schematic diagram of the material detection system illustrated in FIG. 1.

With reference to FIG. 2, system 12 includes a light source 100, a control circuit 95, and a light detector 80. A light source 100 generates a narrow beam of light 50 which passes through conduit or tube 14. After passing through tube 14, light 50 impinges on detector 80.

Light source 100 preferably comprises a light emitting diode (LED) 40, the LED being driven by an oscillator 20 coupled to a precision current source 30. The LED 40 emits narrow beam of light 50, preferably less than ten degrees wide and no more than twenty-five degrees wide. LED 40 is chosen such that the width, frequency range, and intensity of the light beam 50 which it generates are suitable for detecting various materials.

In a preferred embodiment, LED 40 has a power rating of 27–94 mW/sr, emits a light beam 50, approximately eight degrees wide, comprising light in the infrared portion of the electromagnetic spectrum (e.g., a wave length of 880 nm or 940 nm). Infrared light is suitable for detecting a wide range of materials because many liquids which are relatively opaque at optical wavelengths are relatively more translucent at infrared wavelengths. Alternatively, a laser, rather than an LED, may be chosen to generate light beam 50. Lasers are typically more expensive than LEDs, but generally produce a more intense light beam 50 at a specific frequency.

Light source 100 is oriented such that light beam 50 impinges on a surface 14A of tube 14, substantially perpendicular to the lengthwise axis of tube 14. Light beam 50 passes through surface 14A of tube 14. Light beam 50 continues being refracted at the interface of surface 14A and whatever material (e.g., liquid 18) may be inside tube 14. After passing through the material in tube 14, light beam 50 is again refracted as it travels through surface 14B of tube 14, substantially opposite surface 14A. Finally, light beam 50 impinges detector 80. So that light beam 50 may pass through tube 14, it comprises a material (e.g., polypropylene, glass, plastic, etc.) which is at least partially translucent to the frequency characteristics of light beam 50.

As previously mentioned, light 50 is refracted as it passes through tube 14 and whatever material (e.g., liquid 18) may be inside tube 14. Light 50 is refracted at an angle related to the difference of the refractive index of the material comprising tube 14 and the refractive index of whatever material (e.g., liquid 18) may be inside tube 14. It should be noted that refraction occurs as light 50 passes through surface 14A and also as light 50 subsequently passes through surface 14B. Thus, by increasing the difference in refractive indexes through introduction of material into tube 14, the width of light beam 50 is increased. In the preferred embodiment, a baseline can be established from the width of light beam 50 as it exits surface 14B having been refracted by the presence of air inside tube 14. Subsequently, detecting a width of light beam 50 different than the established baseline will indicate the presence of a material other than air in tube 14. If beam 50 has been refracted by a material with a higher refractive index than air, the width of beam 50 will be greater than the established baseline.

Beam 50 strikes or impinges on detector 80 which preferably comprises an active surface 81. Detector 80 is coupled to control circuit 95. Detector 80 is preferably a photodiode with a 0.09×0.09 inch (e.g., has an area of 0.008 inches squared) or larger active surface 81. Detector 80 has a frequency response tuned to the frequency emitted by LED 40.

Active surface 81 comprises a photosensitive surface oriented substantially opposite light source 100 such that beam 50 impinges on active surface 81 substantially perpendicular angle. Preferably, active surface 81 comprises a large-surface-area photodiode. Surface 81 is chosen such that its range of detectable frequencies substantially includes the frequency or range of frequencies of beam 50. Alternately, if detection of a fluorescent material is desired, surface 81 can be chosen such that its range of detectable frequencies includes the frequency or frequencies at which the fluorescent material re-radiates. Surface 81 generates a signal proportional to the percentage of active surface area 81 impinged by detectable radiation, beam 50. When a material with a higher refraction index than air is inside tube 14, the width of beam 50 impinging on surface 81 will be larger than if air filled tube 14. Thus, the percentage of active surface area 81 impinged by beam 50 will be correspondingly larger when liquid 18 is present within tube 14.

Control circuit 95 includes an amplifier 90, a threshold detection circuit 93, and a relay 150. An output signal from surface 81 is received by amplifier 90, preferably an operational amplifier, which amplifies the signal. Preferably, amplifier 90 is coupled to a threshold-detection circuit 93. The combination of amplifier 90 and detector 80 can be contained in a OPT101 device manufactured by Burr Brown Corporation.

Threshold detection circuit 93 can comprise a high-level detection reference 110 coupled to non-inverting input of a comparator 140, and a low level detection reference 120 coupled to an inverting input of a comparator 130. Low-level reference 120 and high-level reference 110 can be resistive devices and are both preferably adjustable to allow variable calibration of threshold-detection circuit 93. The amplified signal from amplifier 90 is coupled to both a non-inverting input of comparator 130 and an inverting input of comparator 140. The outputs of comparator 130 and comparator 140,are coupled together and provide a comparator signal to a diode 98. Thus, if the amplified signal is below high-level detection reference 110 and above low-level reference 120, indicating that the percentage of active surface area 81 impinged by beam 50 is consistent with air being present in tube 14, the comparator signal is high. Thus, if air is present in tube 14, the comparator signal is high.

Conversely, if a material (liquid 18) is present in tube 14 which blocks beam 50 sufficiently such that the amplified signal is below the low-level reference 120, the comparator signal (driven by comparator 130) is low. Further, when a material (liquid 18) is present in tube 14 with a higher refractive index than air, the amplified signal from amplifier 90 is above the high-level reference 110 causing the comparator signal (driven by comparator 140) to be low. Thus, if either an opaque or a non-opaque liquid 18 is present in tube 14, the comparator signal is low. Comparators 130 and 140 have outputs configured so the comparator signal is low if either comparator 130 or 140 provides a low signal.

Detection circuit 93, including comparators 130 and 140, operates as a window comparator which detects when the amplified signal is between a high and a low threshold. When the amplified signal is between the high threshold and low threshold, the absence of liquid 18 in tube 14 is detected. Preferably, the high threshold level is approximately 01.2 V, and low threshold level is approximately 0.8 V.

Comparator signal is coupled to relay trip circuit 144. The output from relay trip circuit 144 is coupled to relay switch 172. Relay trip circuit 144 can be coupled to an external capacitor to provide time delay. Relay 150 preferably comprises relay trip circuit 144 and relay switch 172 and provides a TTL level output.

Figure 3:
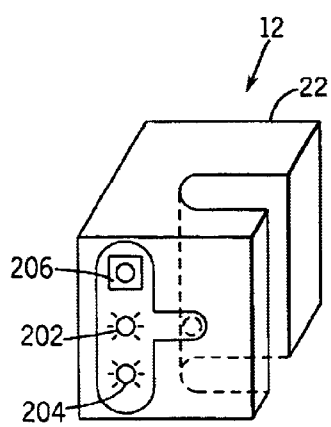
FIG. 3 is a detailed perspective front view of the material detection system illustrated in FIG. 1.

With reference to FIG. 3, system 12 is included in an integral package 22 having a height of 1.25 inches, a width of 1.25 inches and a depth of 1.6 inches. System 12 includes a slot dimensioned to receive 0.25 inch diameter tubing, such as, tube 14. Alternatively, other package and slot sizes and types can be utilized. For example, a package having a hinged structure rather than an open slot can be utilized. Preferably, package 12 includes LED indicators 202 and 204 to indicate the power and detection status associated with system 12. In addition, potentiometer 206 can be provided to adjust detection sensitivity levels. Package 12 can include control circuit 95, light source 100, and photosensitive surface 81. Control circuit 95 can he provided in a potting compound within package 12.

Figure 4:
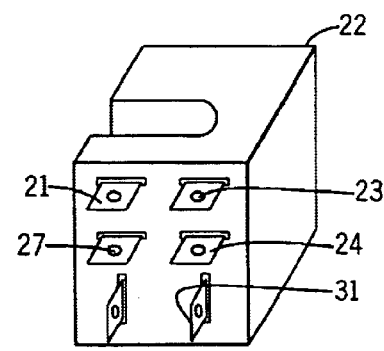
FIG. 4 is a detailed perspective rear view of the liquid detection system illustrated in FIG. 1.

With reference to FIG. 4, package 22 has a footprint associated with a standard relay socket including relay terminals 21 and 23, power terminals 27 and 29, and terminal 31. The footprint allows package 22 to be easily inserted into existing designs.

It is understood that while the detailed drawings, specific examples, and particular values given provide a preferred exemplary embodiment of the present invention, the preferred exemplary embodiment is for the purpose of illustration only. The method and apparatus of the invention is not limited to the precise details and conditions disclosed. For example, although the comparator-based control circuit is discussed, other techniques can be utilized to determine whether the output signal represents the presence or absence of a material. Various changes may be made to the details disclosed without departing from the spirit of the invention which is defined by the following claims.

What is claimed is:

1. An apparatus for detecting a material in a translucent conduit, comprising:
   a light source disposed adjacent to a first outside surface of the conduit and generating a narrow beam of light;
   a light detector having an active surface disposed adjacent to the conduit and aligned to receive light from the light source, the light detector being operable to detect a surface area of light which impinges on the active surface and to provide an output signal proportional thereto, whereby the material in the conduit is detected by comparing the output signal to a threshold window.

2. The apparatus of claim 1, wherein the light source comprises a light emitting diode.

3. The apparatus of claim 2, wherein the narrow beam of light diverges from the diode by no more than 20 degrees.

4. The apparatus of claim 1, wherein the light source comprises a laser.

5. The apparatus of claim 1, wherein the light detector comprises a large surface area photodiode.

6. The apparatus of claim 1, further including means for determining that the output signal is within or outside the threshold window.

7. The apparatus of claim 5, further including a relay operable to activate when the output signal is above the threshold window and to close when the output signal is below the threshold window.

8. The apparatus of claim 1, including a means for securing the apparatus to the conduit such that the narrow beam of light is directed substantially perpendicular to a lengthwise axis of the conduit.

9. The apparatus of claim 1, wherein the light source comprises a precision current source.

10. A method of detecting a material in a translucent conduit, the method comprising:
    providing a narrow light beam through the conduit;
    detecting a width of the narrow light beam exiting the conduit;
    providing an output signal, wherein the output signal is proportional to the width of the narrow light beam detected in the detecting step; and
    determining a presence of the material by comparing the output signal to a threshold window.

11. The method of claim 10, wherein the narrow light beam is provided substantially perpendicular to a lengthwise axis of the conduit.

12. A system for detecting a presence of a material, comprising:
    a first translucent surface;
    a second translucent surface being substantially in apposition to the first translucent surface, the material being located between the first translucent surface and the second translucent surface;
    a narrow-beam light source, the light source disposed adjacent the first surface;

a light detector having an active surface disposed adjacent the second surface and along an axis defined by the light source and substantially in apposition to the light source, the light detector being operable to detect the surface area of light which impinges on the active surface and to provide an output signal proportional thereto; and whereby the light from the light source which passes through the material interposed between the first and second surfaces is refracted and impinges on the active surface, the output signal indicates a presence of the material when the output signal is above or below a threshold window.

13. The apparatus of claim 12, further comprising a package having a relay footprint, the package housing the system.

14. The apparatus of claim 12, wherein the narrow beam of light diverges from the light source by no more than 20 degrees.

15. The apparatus of claim 12, wherein the light source comprises a laser.

16. The apparatus of claim 12, wherein the light detector comprises a large surface area photodiode.

17. The apparatus of claim 12, including a means for determining that the output signal is within a threshold window or outside a threshold window.

18. The apparatus of claim 12, wherein the first surface comprises half of a longitudinal surface of a length of the translucent conduit and the second surface comprises the remaining half of the conduit.

19. The apparatus of claim 12, wherein the light source comprises a precision current source.

20. The apparatus of claim 12, including a means for maintaining the relative positions of the light detector, the first surface, the second surface, and the light detector.

\* \* \* \* \*